(12) United States Patent  
Murashita et al.

(10) Patent No.: US 8,216,144 B2
(45) Date of Patent: Jul. 10, 2012

(54) ULSTRASOUND DIAGNOSTIC APPARATUS AND VOLUME DATA PROCESSING METHOD

(75) Inventors: Masaru Murashita, Mitaka (JP); Masashi Nakamuira, Mitaka (JP)

(73) Assignee: Hitachi Aloka Medical, Ltd., Tokyo (JP)

(*) Notice: Subject to any disclaimer, the term of this patent is extended or adjusted under 35 U.S.C. 154(b) by 1273 days.

(21) Appl. No.: 11/939,935

(22) Filed: Nov. 14, 2007

(65) Prior Publication Data

US 2008/0114244 A1    May 15, 2008

(30) Foreign Application Priority Data

Nov. 14, 2006  (JP) .................................. 2006-307663
Apr. 12, 2007  (JP) .................................. 2007-104733

(51) Int. Cl.
A61B 8/00 (2006.01)
(52) U.S. Cl. ...................................................... 600/443
(58) Field of Classification Search .................. 600/437, 600/443
See application file for complete search history.

(56) References Cited

U.S. PATENT DOCUMENTS

| | | | |
|---|---|---|---|
| 6,545,678 B1 * | 4/2003 | Ohazama | 345/427 |
| 6,687,392 B1 | 2/2004 | Touzawa et al. | |
| 2002/0102023 A1 | 8/2002 | Yamauchi | |
| 2003/0198372 A1 | 10/2003 | Touzawa et al. | |
| 2004/0097808 A1 | 5/2004 | Murashita | |

FOREIGN PATENT DOCUMENTS

| | | | |
|---|---|---|---|
| EP | 1720039 A2 | 11/2006 | |
| JP | 11164834 A | * | 6/1999 |
| JP | 10305033 A | 11/1999 | |
| JP | 2000107183 A | 4/2000 | |
| JP | 2000296129 A | 10/2000 | |
| JP | 2002224116 A | 8/2002 | |
| JP | 2002330968 A | 11/2002 | |
| JP | 2004159997 A | 6/2004 | |
| WO | WO 01/01864 A1 | 1/2001 | |

OTHER PUBLICATIONS

European Search Report dated Mar. 18, 2008, issued in corresponding European Patent Application No. 07020529.
Sampath, V.; "Transrectal Ultrasound Image Processing for Brachytherapy Applications";, RIT Digital Media Library, pp. 1-60, Sep. 25, 2006, XP002471675.

(Continued)

*Primary Examiner* — Jacqueline Cheng
(74) *Attorney, Agent, or Firm* — Westerman, Hattori, Daniels & Adrian, LLP

(57) ABSTRACT

An ultrasound diagnosis apparatus capable of extracting an object tissue within a living body with high precision is provided. A row of reference cross sections is set with regard to volume data. The row of reference cross sections includes a plurality of manual tracing reference cross sections and the remaining sections, i.e. a plurality of automatic tracing reference cross sections. With regard to the manual tracing reference cross sections, manual tracing processing and automatic correction processing is applied. With regard to the automatic tracing reference cross sections, automatic generation processing and automatic correction processing for interpolation tracing lines is applied. Finally, the object tissue is extracted or the volume thereof is calculated based on a plurality of tracing lines. When the similarity between shapes of adjacent manual tracing lines is small, one or a plurality of manual tracing lines may be additionally provided between these tracing lines.

13 Claims, 15 Drawing Sheets

OTHER PUBLICATIONS

Tamura, S. et al; Plan-Based Boundary Extraction and 3-D Reconstruction for Orthogonal 2-D Echocardiography; Pattern Recognition, vol. 20, No. 2, pp. 155-162, 1987, XP009018444.

Baroni, M. et al.; "Contour Definition and Tracking in Cardiac Imaging through the Intergration of Knowledge and Image Evidence"; Annals of Biomedical Engineering, vol. 32, No. 5, pp. 688-695, May 2004, XP002471673.

Landry, A. et al.; "Measurement of Carotid Plaque Volume by 3-Dimensional Ultrasound"; Stoke; A Journal of Cerebral Circulation, vol. 35, No. 4, pp. 864-869, Apr. 2004, XP002471674.

* cited by examiner

40 : SECTIONAL DATA

41 : FETUS

44 : VOLUME DATA

| TYPE | CONDITION | SPECIFIC EXAMPLES |
|---|---|---|
| THRESHOLD VALUE DETERMINATION | IF α IS α1 OR LESS, ADD ONE CROSS SECTION | |
| STEPWISE THRESHOLD VALUE DETERMINATION | α: α2~α3 → ADD ONE CROSS SECTION<br><br>α: α3~α4 → ADD TWO CROSS SECTIONS<br><br>α: α4 OR LESS → ADD THREE CROSS SECTIONS | |
| DYNAMIC DISTRIBUTION | SPECIFY CROSS SECTION PAIR WITH MINIMUM α (OR MINIMUM CORRECTED α), ADD ONE CROSS SECTION<br><br>REPEAT THIS PROCESS (k TIMES) WHILE ADDTING Δα TO MINIMUM α | |

Fig. 22

ULTRASOUND DIAGNOSTIC APPARATUS AND VOLUME DATA PROCESSING METHOD

BACKGROUND

1. Technical Field

The present invention relates to an ultrasound diagnostic apparatus and a volume data processing method, and more particularly to specification or measurement of an object tissue within a three-dimensional space.

2. Related Art

A three-dimensional space (a three-dimensional data acquisition space) can be formed by scanning a scanning plane, which is formed by scanning an ultrasound beam, in the direction orthogonal to the scanning plane. A Disk Summation method is conventionally known as a method for extracting an object tissue existing within a three-dimensional space and calculating the volume thereof. With this conventional method, each of a plurality of slice data items which are aligned across the object tissue is displayed as a tomographic image, and the outline of the object tissue is manually traced on each tomographic image, enabling the cross sectional area in each slice to be calculated. Then, the cross sectional area and the thickness (an interval between cross sections) for each slice is used to calculate an element volume of each portion (each disc) in the object tissue. By summing these element volumes, a total volume of the object tissue is obtained. According to this conventional method, the volume of the object tissue cannot be obtained with a high precision unless the number of slice data items (i.e. the number of cross sections to be measured) is increased. On the other hand, the burden of a user increases when manual tracing is required with respect to a great number of slice data items. While application of automatic tracing in place of manual tracing with respect to each cross section may be considered, if the outline includes an unclear portion, automatic tracing cannot be performed or the reliability of tracing results is decreased.

JP2004-159997A describes processing for extracting a tissue (cardiac chamber or the like) existing within a three-dimensional space. JP2002-224116A describes extraction of a tissue by using an outline model. JP11-164834A describes technology of correcting a manual tracing result. JP10-305033A, JP2002-330968A, JP2000-107183A, and JP2000-296129 all describe technology of calculating a volume of a tissue.

With regard to specification or measurement of an object tissue, technologies which sufficiently satisfy the demand for achieving a high precision and lessening the burden of a user have not yet been achieved. None of the documents described above describes a combined technology which allows realization of the advantages of both manual tracing and automatic tracing in situations in which the outline of a tissue includes both clear and unclear portions. For example, with regard to the placenta within a uterus during the later weeks of pregnancy, a region of the placenta in contact with the uterus has a small difference in brightness in its ultrasound image whereas a region of the placenta in contact with the amniotic fluid has a significant difference in brightness in its ultrasound image. For the above reasons, there has been a demand for technology which makes it possible to reduce the burden on a user while increasing precision when tracing a placenta in an ultrasound image.

SUMMARY

The present invention advantageously provides an apparatus and a method which enables improving the precision of specification or measurement of an object tissue without imposing a significant burden on a user.

An ultrasound diagnostic apparatus according to an aspect of the invention includes a data acquisition section which performs transmission and reception of ultrasound with respect to a three-dimensional space including an object tissue to acquire volume data; a representative cross section processing section which, when a plurality of manual tracing lines are formed on a plurality of representative cross sections which are set with regard do the object tissue, applies first correction processing to each manual tracing line; a non-representative cross section processing section which forms, by interpolation processing based on a plurality of manual tracing lines to which the first correction processing has been applied, a plurality of interpolation tracing lines on a plurality of non-representative cross sections which are set with regard to the object tissue, and applies second correction processing to each interpolation tracing line; and a unit which extracts object tissue data from the volume data or calculates a volume of the object tissue, based on rows of tracing lines formed of a plurality of manual tracing lines to which the first correction processing has been applied and a plurality of interpolation tracing lines to which the second correction processing has been applied.

Preferably, a set of cross sections formed of a plurality of cross sections is set with respect to an object tissue (data corresponding to an object tissue) within volume data. In this case, the set of cross sections is preferably set so as to cover a whole object tissue. The set of cross sections may correspond to a set of scanning planes formed of a plurality of scanning planes or may be set independently from the set of scanning planes. In the set of cross sections, intervals between individual cross sections may be uniform or non-uniform. With regard to a portion in the object tissue where its shape significantly changes, a density of cross sections may be increased. In any case, the set of cross sections is formed by including a plurality of representative cross sections and a plurality of non-representative cross sections. When a plurality of representative cross sections are defined with respect to the object tissue, a manual tracing line is formed on each representative cross section. With the above structure, in which manual tracing is performed with regard to a small number of representative cross sections, not all the cross sections, the burden of a user can be reduced. Then, first correction procession is applied to each manual tracing line. The first correction processing includes determination of necessity of correction and execution of correction. With regard to each manual tracing line, a determination at least as to whether or not correction is necessary is made. As such, each manual tracing line is automatically corrected as required. For example, automatic tracing can be applied with regard to a portion of an object tissue having a clear outline (boundary). In addition, because automatic tracing can generally be performed with a higher precision than manual tracing (i.e., tracing results accounting for fine unevenness are more likely to be obtained by automatic tracing), the results of manual tracing can be automatically corrected entirely or partially. (Consequently, manual tracing lines which has been corrected can be obtained.) In this case, clearness of the outline of the object tissue can be used as a criterion for determining whether or not application of correction processing is necessary. When the manual tracing lines to which the first correction processing has been applied are formed on the plurality of representative cross sections, respectively, interpolation tracing lines can be automatically formed in an easy manner on the individual non-representative cross sections on the basis of the manual tracing lines thus formed. For example, between two manual tracing lines (adjacent manual tracing lines) on two adjacent representative cross sections (a pair of adjacent representative cross sections), i.e. on one or a plurality of non-representative cross sections, one or a plurality of interpolation tracing lines are automatically formed by interpolation processing. Thereafter, a second correction processing is applied to each interpolation tracing line. The second correction processing, similar to the first correction processing described above, includes determination of necessity of correction and execution of correction. Specifically, each interpolation tracing line is corrected based on the actual tissue outline as required, thereby obtaining an interpolation tracing line which has been corrected. As such, based on a row of tracing lines formed on a plurality of cross sections (including the plurality of manual tracing lines after the first correction processing and the plurality of interpolation tracing lines after the second correction processing), a surface shape of the object tissue can be imitated, and a three-dimensional image representing the surface of the object tissue can be formed or a volume of the object tissue can be calculated. With the above structure, because the individual manual tracing lines and the individual interpolation tracing lines can be corrected based on the actual outline of the tissue (and as required), the precision in calculation and measurements can be increased. In other words, with the above method, manual tracing and automatic tracing can be organically combined so that the advantages of both types of processing can efficiently be obtained.

Preferably, the representative cross section processing section includes a selection section which selects the plurality of representative cross sections from a set of cross sections which is set with respect to the object tissue, a unit which receives a tracing input from a user with respect to each representative cross section which is selected, and a first correction processing section which, for the first correction processing, determines whether or not correction can be applied for each point on each manual tracing line and corrects a position of a point which is determined to be correctable based on an actual tissue outline. The representative cross sections are designated automatically or designated by a user. The number of cross sections forming a set of cross sections or the number of representative cross sections in a set of cross sections is designated automatically or designated by a user. Tracing of a tissue outline by a user is normally performed on a tomographic image. While there are cases wherein fine unevenness cannot be sufficiently traced when drawing manual tracing lines, as long as the tissue outline is clear (or distinguishable), the fine unevenness can be traced with high precision by automatically correcting the manual tracing results (i.e. additional application of automatic tracing). Alternatively, when it is not necessary to perform faithful manual tracing with respect to such fine unevenness, the burden on a user can be reduced.

Preferably, the first correction processing section determines whether or not correction can be performed by setting a cross line with regard to each point and performing edge detection on the cross line. For edge detection, it is preferable that changes in the brightness value (a differential value) or the like are considered.

Preferably, the non-representative cross section processing section includes a unit which forms an interpolation tracing line on each non-representative cross section by interpolation processing based on a plurality of manual tracing lines to which the first correction processing has been applied, and a second correction processing section which, for the second correction processing, determines whether or not correction can be performed for each point on each interpolation tracing line and corrects a position of a point which is determined to be correctable based on an actual tissue outline. With this structure, the interpolation tracing lines are automatically generated on the respective non-representative cross sections, and then each interpolation tracing line is corrected based on the actual tissue outline, so that the tracing results can be obtained with high precision. As no manual operations are necessary for the non-representative cross sections, the burden on the user can be lessened. Further, because the interpolation tracing lines are not only generated but also corrected based on the actual tissue outline, reliability of the interpolation processing results can be increased.

Preferably, the second correction processing section determines whether or not correction can be performed by setting a cross line with regard to each point and performing edge detection on the cross line. Preferably, the ultrasound diagnostic apparatus includes a unit which receives designation of a base line extending through the object tissue, and a unit which sets a set of cross sections which are arranged in a direction of the base line and which are orthogonal to the base line, and the plurality of representative cross sections and the plurality of non-representative cross sections are determined from the set of cross sections. With this structure, a set of cross sections is preset prior to tracing, and some cross sections forming the set are designated as the representative cross sections, respectively, and other cross sections are designated as the non-representative cross sections, respectively. However, it is also possible that a plurality of representative cross sections and a plurality of non-representative cross sections are set stepwise, so that a set of cross sections is consequently defined.

A method according to another aspect of the present invention includes storing volume data acquired by performing transmission and reception of ultrasound with respect to a three-dimensional space including an object tissue; receiving a plurality of manual tracing operations with respect to a plurality of representative cross sections which are set with regard to the object tissue; performing correction processing by determining whether or not position correction can be performed, based on an actual tissue outline, with regard to each point on each manual tracing line formed on each of the representative cross sections and each point on each interpolation tracing line formed on each of non-representative cross sections which are set with regard to the object tissue and correcting a position of a point which is determined to be correctable; and extracting the object tissue or calculating a volume of the object tissue based on a row of a plurality of interpolation tracing lines and a plurality of manual tracing lines to which the correction processing has been applied.

An ultrasound diagnostic apparatus according to a further aspect of the invention includes a data acquisition section which performs transmission and reception of ultrasound with respect to a three-dimensional space including an object tissue to acquire volume data; a representative cross section processing section which, when a plurality of manual tracing lines are formed on a plurality of representative cross sections which are set with regard to the object tissue, applies first correction processing to each manual tracing line; a similarity calculation section which calculates similarity for each pair of adjacent manual tracing lines in a plurality of manual tracing lines before or after the first correction processing; an additional representative cross section setting section which adds one or a plurality of additional representative cross sections in addition to the plurality of representative cross sections based on the similarity for each pair of adjacent manual tracing lines; an additional representative cross section processing section which applies the first correction processing to one or a plurality of manual tracing lines formed on the one or a plurality of additional representative cross sections; a non-representative cross section processing section which forms, by interpolation processing based on a plurality of manual tracing lines to which the first correction processing has been applied, a plurality of interpolation tracing lines on a plurality of non-representative cross sections which are set with regard to the object tissue, and applies second correction processing to each interpolation tracing line; and a unit which extracts object tissue data from the volume data or calculates a volume of the object tissue, based on rows of tracing lines formed of a plurality of manual tracing lines to which the first correction processing has been applied and a plurality of interpolation tracing lines to which the second correction processing has been applied.

With the above structure, measurement of an object tissue can be performed by a combination of manual tracing, interpolation processing, and automatic tracing. In particular, one or a plurality of additional representative cross sections are set as required between a pair of adjacent representative cross sections. Namely, when a pair of adjacent manual tracing lines are significantly dissimilar (with respect to a portion of a tissue where the shape changes significantly), one or a plurality of manual tracing lines can be additionally generated between the pair of adjacent manual tracing lines. As such, because the representative cross sections can be set with a high density in a portion of an object tissue where the shape changes significantly, for example, (i.e. because the manual tracing lines are formed with a high density,) the precision in measuring the object tissue can be increased. Here, as the necessity of such addition setting is determined in accordance with the level of similarity, the number of the representative cross sections (the original representative cross sections and the additional representative cross sections) can be minimized, so that an increase in the burden imposed by the manual tracing can be prevented. With the above structure, a plurality of original manual tracing lines and one or a plurality of additional manual tracing lines are generated. The calculation of similarity may be performed with regard to a plurality of original manual tracing lines prior to the first correction processing or with regard to a plurality of original manual tracing lines after the first correction processing. In the former case, after the addition processing, the first correction processing is applied to all the manual tracing lines. Further, in the latter case, the first correction processing for the first time which is applied to the plurality of original manual tracing lines and the first correction processing for the second time which is applied to the plurality of additional manual tracing lines are performed stepwise.

Preferably, the similarity calculation section calculates the similarity by performing cross correlation operation between two manual tracing lines forming each pair of adjacent manual tracing lines. With the cross correlation operation, information representing the degree of similarity of the outline shape between adjacent manual tracing lines can be obtained.

Preferably, the additional representative cross section setting section adds the one or a plurality of additional representative cross sections between a pair of adjacent representative cross sections for which the similarity satisfies a predetermined addition condition. Preferably, the additional representative cross section setting section determines the number of additional representative cross sections to be added in accordance with the degree of the similarity.

A method according to another aspect of the present invention includes storing volume data obtained by performing transmission and reception of ultrasound with respect to a three-dimensional space including an object tissue; receiving a plurality of manual tracing operations with respect to a plurality of representative cross sections which are set with regard to the object tissue; when one or a plurality of additional representative cross sections are set in addition to the plurality of representative cross sections, receiving one or a plurality of manual tracing operations with respect to the one or a plurality of additional representative cross sections; performing correction processing by determining whether or not position correction can be performed, based on an actual tissue outline, with regard to each point on each manual tracing line formed on each of the representative cross sections, on each manual tracing line formed on each of the additional representative cross sections, and on each interpolation tracing line formed on each of non-representative cross sections which are set with regard to the object tissue and correcting a position of a point which is determined to be correctable; and extracting the object tissue or calculating a volume of the object tissue based on a row of a plurality of interpolation tracing lines and a plurality of manual tracing lines to which the correction processing has been applied.

BRIEF DESCRIPTION OF THE DRAWINGS

Preferred embodiments of the present invention will be described in detail based on the following figures, wherein:

FIG. 22 is a view for explaining some methods of adding cross sections; and

DETAILED DESCRIPTION

Preferred embodiments of the present invention will be described in detail with reference to the accompanying drawings.

Figure 1:
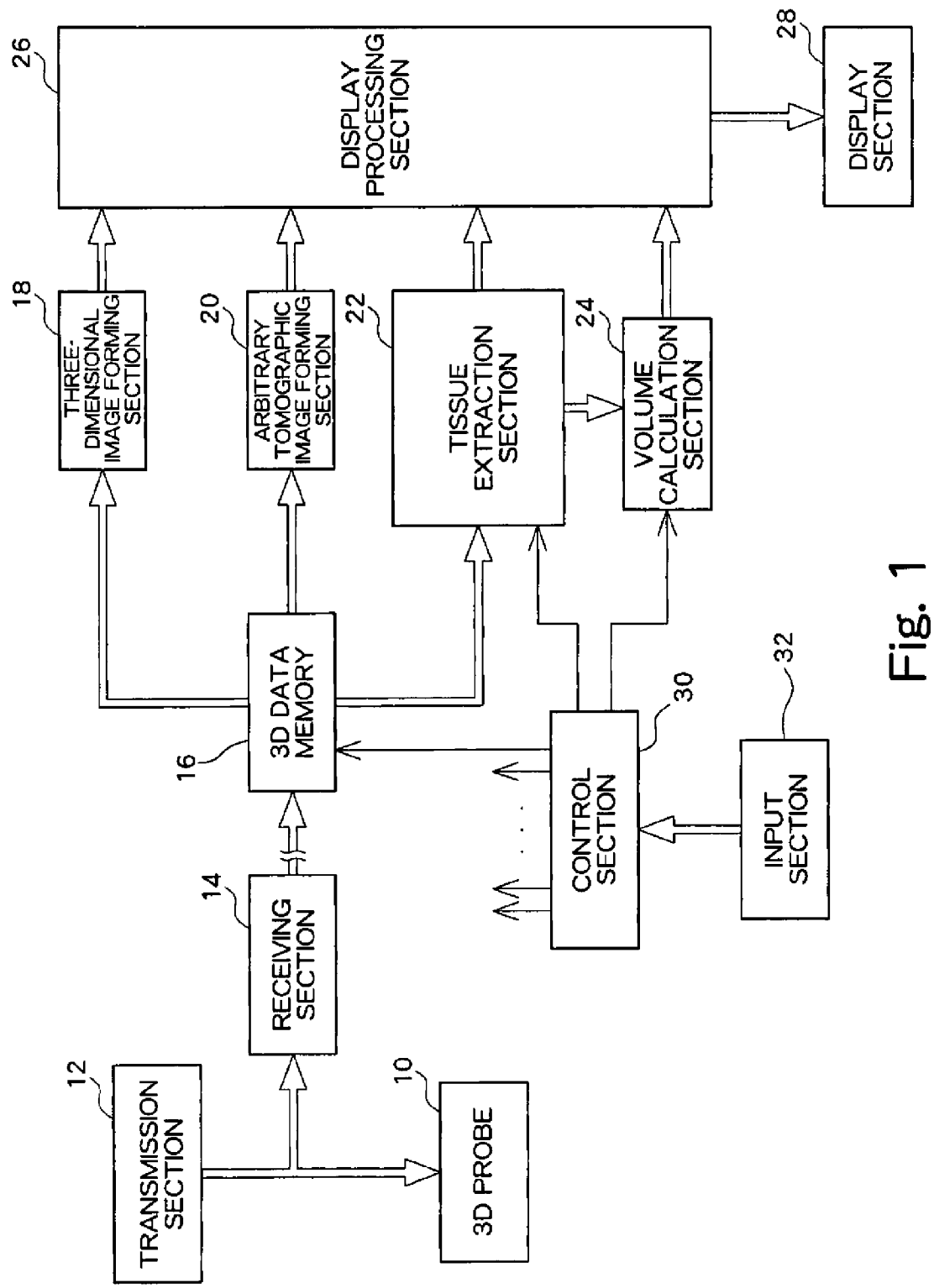
FIG. 1 is a block diagram showing an ultrasound diagnostic apparatus according an embodiment of the present invention.

FIG. 1 is a block diagram showing the overall structure of an ultrasound diagnosis apparatus according to an embodiment of the present invention. This ultrasound diagnosis apparatus is intended for use in the medical field, and, in particular, has a function of extracting an object tissue within a living body and calculating the volume thereof. The object tissue may include a placenta, a malignant tumor, a gallbladder, a thyroid gland, and so on. In the following examples, processing of extracting a placenta as an object tissue will be described.

Referring to FIG. 1, a 3D (three-dimensional) probe 10 is an ultrasound transmitter/receiver which is used in contact with a body surface or used in a state where it is inserted into cavities of humans. In this embodiment, the 3D probe 10 includes a 2D (two-dimensional) array transducer which is composed of a plurality of transducer elements arranged in the first and second directions. An ultrasound beam is formed by the 2D array transducer and is scanned two-dimensionally, so that a three-dimensional echo data capturing space is formed as a three-dimensional space. More specifically, the three-dimensional space is formed as an assembly of a plurality of scanning planes each formed by scanning an ultrasound beam one dimensionally. A mechanism for mechanically scanning a 1D array transducer may be provided, in place of the 2D array transducer, for forming a similar three-dimensional space.

A transmission section 12 functions as a transmitting beam former. The transmission section 12 supplies a plurality of transmitting signals which are delayed to the 2D array transducer, and thus a transmitting beam is formed. Reflected waves from the living body are received by the 2D array transducer, which thereby outputs a plurality of receiving signals to a receiving section 14. The receiving section 14 executes alignment and summation processing with respect to the plurality of receiving signals, thereby outputting a receiving signal (beam data) having been subjected to alignment and summation processing. The receiving signal is then subjected to predetermined signal processing including detection, logarithmic transformation, and so on. The beam data which is a receiving signal having been subjected to signal processing is stored in a 3D memory 16.

The 3D data memory 16 includes a three-dimensional memory space corresponding to a three-dimensional space which is a transmission/reception space within a living body. When writing or reading data is performed with respect to the 3D data memory 16, coordinate transformation with regard to each data is executed. In the present embodiment, when writing data in the 3D data memory 16, coordinate transformation from a transmission/reception coordinate system to a memory space coordinate system is performed, whereby volume data which will be described below is formed. The volume data is an assembly of a plurality of frame data items (a plurality of slice data items) corresponding to a plurality of scanning planes. Each frame data is composed of a plurality of beam data items, and each beam data is formed of a plurality of echo data arranged in the depth directions. Here, the 3D data memory 16 and each of the elements which will be described after this 3D data memory 16 can be implemented as special-use hardware or as a software function.

A three-dimensional image forming section 18 executes image processing based on a volume rendering method, for example, based on the volume data stored in the 3D data memory 16, thereby forming a three-dimensional ultrasound image. The image data thus obtained is transmitted to a display processing section 26. An arbitrary tomographic image forming section 20 forms a tomographic image corresponding to an arbitrary cross section within a three-dimensional space which is set by a user. In this case, data array corresponding to the arbitrary cross section is read from the 3D data memory 16, so that, based on the data array thus read, a B mode image is formed as an arbitrary tomographic image. The resulting image data is then transmitted to the display processing section 26.

A tissue extraction section 22, which is a module that executes image processing specific to the present embodiment and which will be described in detail below, extracts an object tissue (object tissue data) existing within the three-dimensional space or the volume data space by using trace processing. In this case, as will be described in detail below, manual tracing processing and interpolation processing are used in combination, and also automatic correction processing is used with respect to the respective processing results. The object tissue data thus extracted is transmitted to the display processing section 26 and used for image display of the object tissue, and, in the present embodiment, is also transmitted to a volume calculation section 24.

The volume calculation section 24 is a module which obtains a volume of an object tissue by using the volume calculation method (Disk Summation Method) described above. More specifically, as a row of tracing lines formed of a plurality of closed loops are formed for the whole object tissue by the tissue extraction section 22, the volume calculation section 24 obtains the volume of the object tissue in an approximate manner based on these tracing lines. In this case, the distance between each closed loops, i.e. between each cross section, is also used. The data of the volume values thus calculated is transmitted to the display processing section 26. Here, the volume calculation method includes, in addition to the Disk Summation Method described above, Average Rotation Method, and so on.

Each of the modules, i.e. the three-dimensional image forming section 18, the arbitrary tomographic image section 20, and the tissue extraction section 22, and so on, functions in accordance with an operation mode selected by a user, and data corresponding to the respective modes are input to the display processing section 26. The display processing section 27 performs image combining processing, coloring processing, and so on, with respect to the input data, and outputs image data which is the processing result. In accordance with the operation mode, a three-dimensional ultrasound image, an arbitrary tomographic image, and so on, and also a three-dimensional image of the extracted tissue, and the volume thereof are displayed in the display section 28. Here, it is possible to display the three-dimensional image of the whole three-dimensional space and the three-dimensional image of the object tissue in a combined manner.

A control section 30 controls the operation of each section shown in FIG. 1, and particularly controls the tissue extraction processing and the volume calculation described above based on the parameters set by a user through an input section 32. The control section 30 also controls data writing to the 3D data memory 16 and so on. The input section 32 is formed of an operation panel including a keyboard, a trackball, and so on. The control section 30 is formed of a CPU, an operation program, and so on. Here, the three-dimensional image processing, the arbitrary tomographic image forming processing, the tissue extraction processing, and the volume calculation may be executed by a single CPU.

Figure 2:
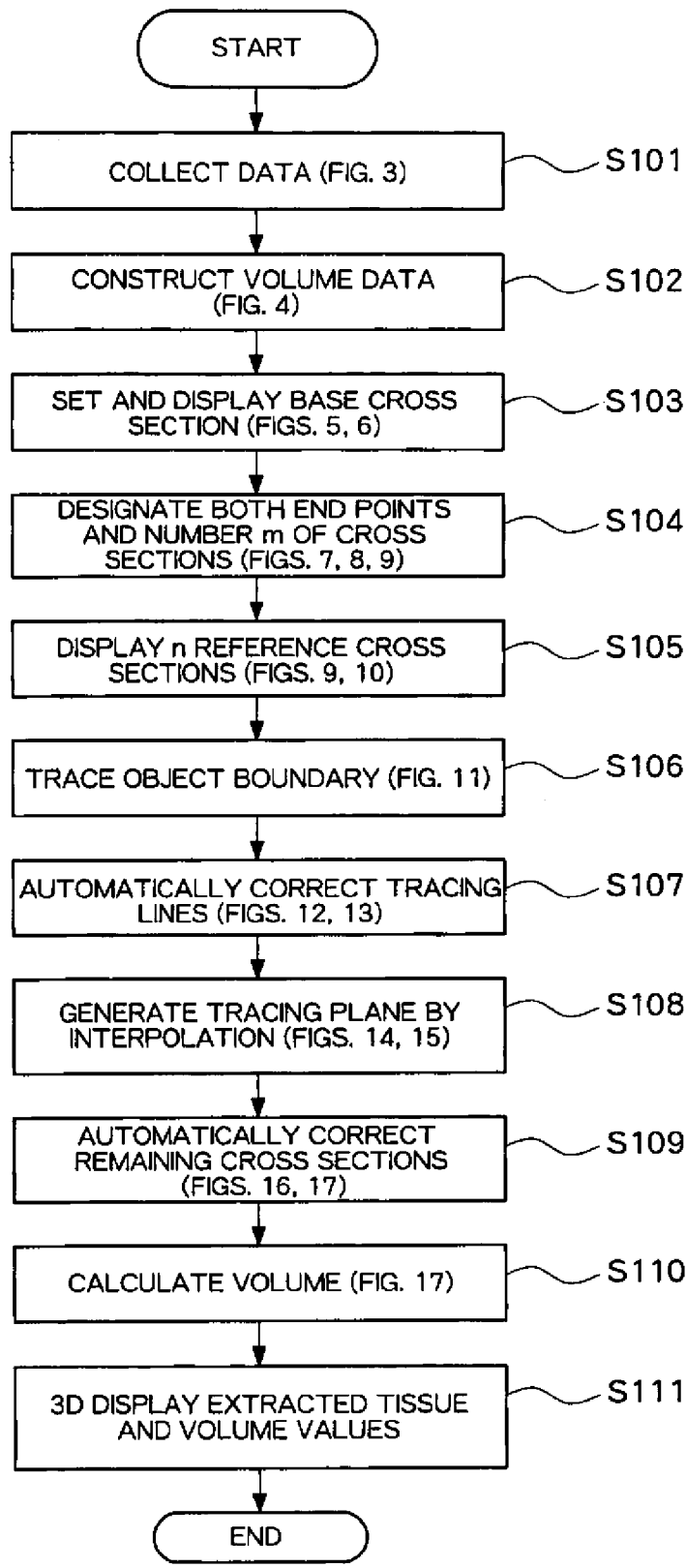
FIG. 2 is a flowchart for explaining processing of extracting an object tissue.

Referring now to FIG. 2 and the subsequent drawings, the processing of extracting an object tissue will be specifically described. FIG. 2 provides a flowchart for the entire process.

Figure 3:
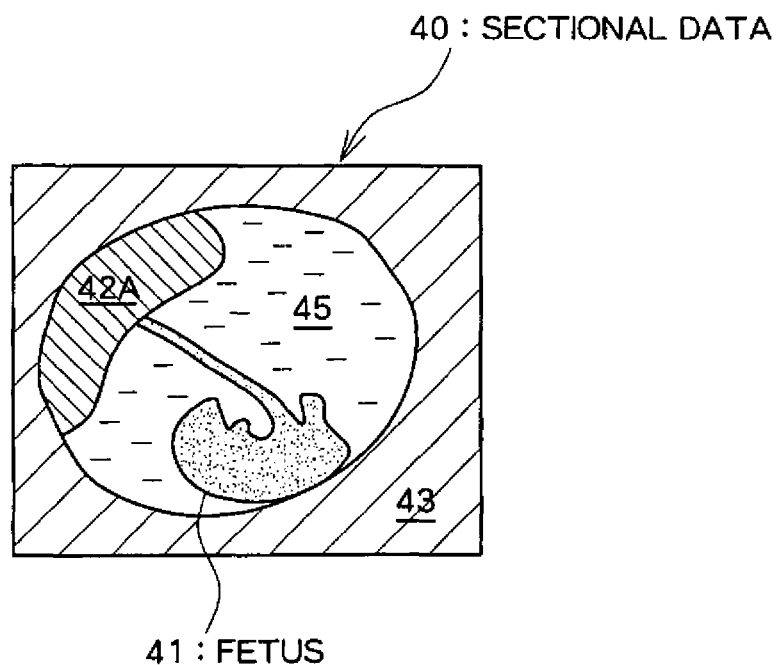
FIG. 3 is a view showing a cross sectional data concerning uterus.

In step S101, data is collected by using the 3D probe described above. In this case, a plurality of scanning planes are formed. FIG. 3 shows sectional data 40 corresponding to one scan plane. In the present embodiment, an object for observation is a placenta, such as that shown in FIG. 3 as cross section 42A. Here, numeral 41 denotes a fetus, numeral 43 denotes a uterus, and numeral 45 denotes amniotic fluid. As shown, the placenta 42A is attached or joined to the inner wall of the uterus 43, and the image on the sectional data 40 at this joining portion, i.e. the boundary portion, shows little difference in brightness and is unclear.

Figure 4:
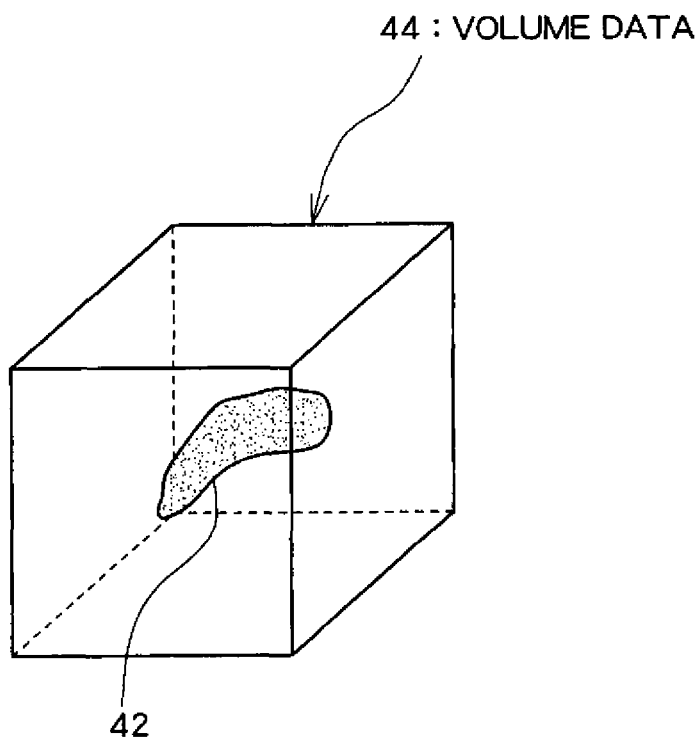
FIG. 4 is a view showing volume data including placenta.

In step S102 of FIG. 2, volume data is assembled in the 3D data memory shown in FIG. 1. Specifically, the sectional data 40 as shown in FIG. 3 is sequentially stored in the 3D data memory 16, whereby a set of volume data is assembled in the memory 16, as shown in FIG. 4. The volume data (or a three-dimensional space) 44 includes a placenta (placental data) 42, with other tissues not shown in FIG. 4.

Figure 5:
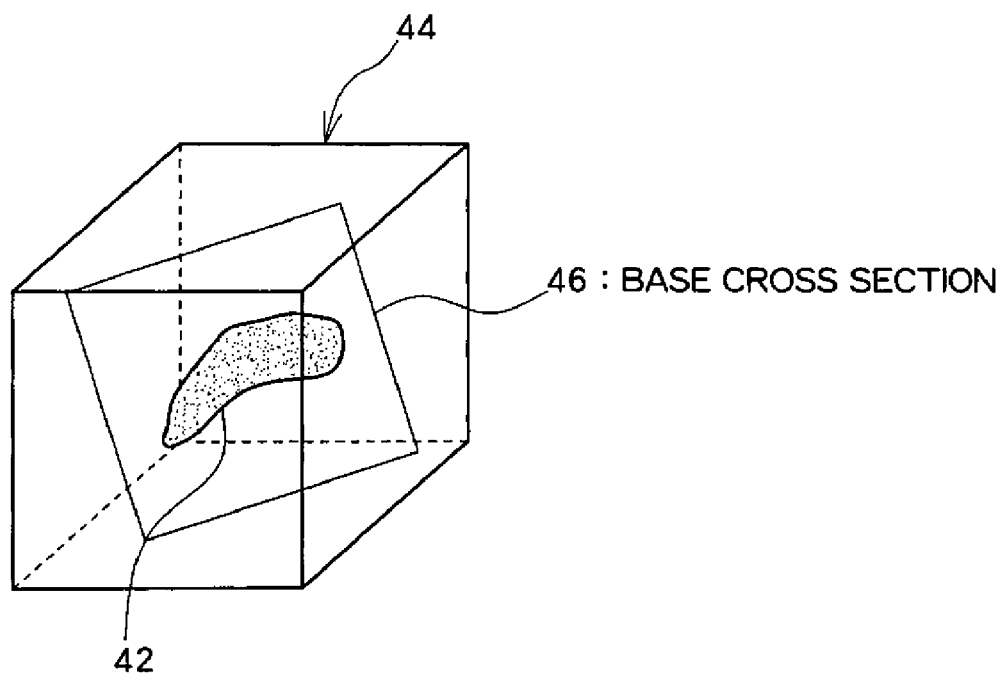
FIG. 5 is a view for explaining setting of a base cross section with respect to volume data.
Figure 6:
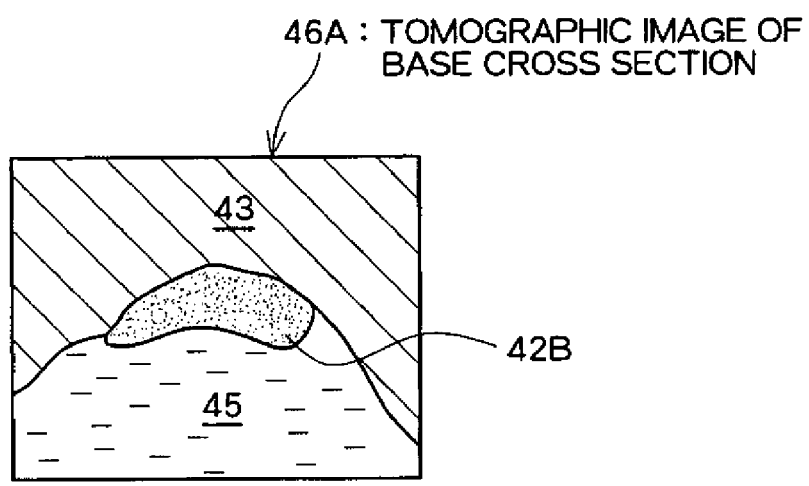
FIG. 6 is a view showing a tomographic image corresponding to the base cross section.

In step S103, while an arbitrary tomographic image is being displayed on the display section, the position of the cross section is approximately adjusted, thereby setting a base cross section 46 as shown in FIG. 5. In this case, it is desirable to position the base cross section 46 such that the whole placenta 42 which is an object tissue appears on the tomographic image, and particularly that the display size of the placenta can be maximized. However, because this base cross section is used for merely determining the basis for setting a row of reference cross sections (a set of cross sections), it is sufficient to set the base cross section 46 such that approximately the entire of the placenta 42 is covered, and strict positioning of the base cross section 46 is not required. FIG. 6 shows, in an enlarged view, a tomographic image 46A corresponding to the base cross section 46. In FIG. 6, (the cross section of) the placenta 42B is attached to (the cross section of) the uterus 43.

Figure 7:
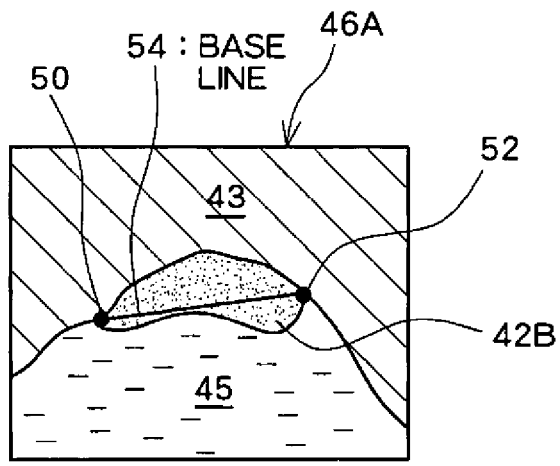
FIG. 7 is a view for explaining setting of a base line on the tomographic image.

In step S104, as shown in FIG. 7, points at both ends of the placenta 42B which is an object tissue are designated by a user on the tomographic image 46A representing the base cross section. In FIG. 7, the points at both ends are designated with numerals 50 and 52. A straight line connecting these points is a base line 54. Further, in step S104, the number m of cross sections forming a row of reference cross sections which will be described below is also set.

Figure 8:
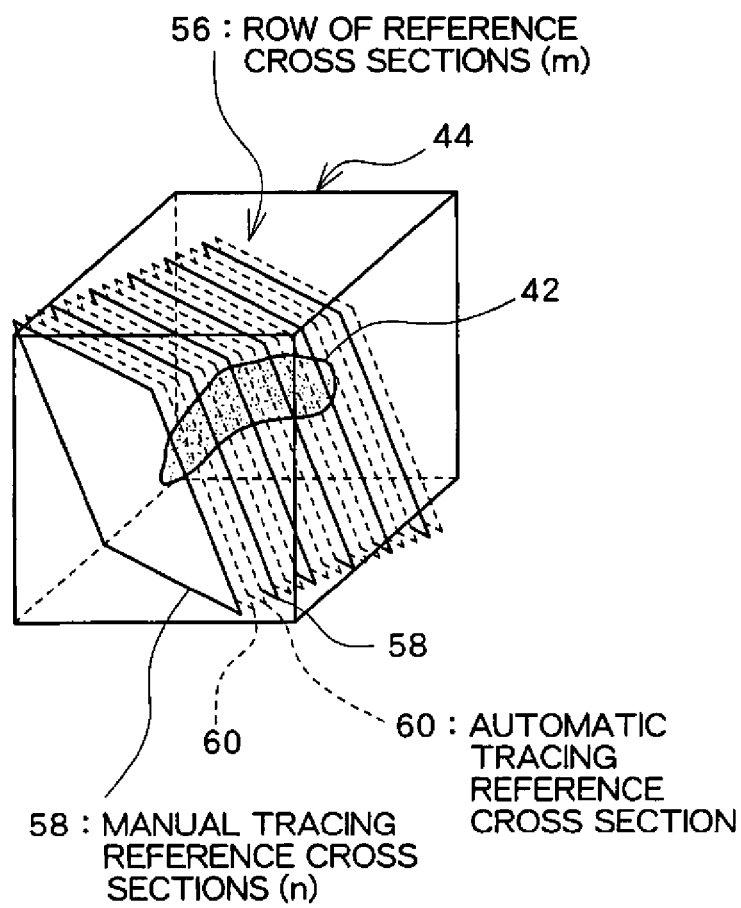
FIG. 8 is a view showing a row of reference cross sections automatically formed using the base line as a basis with respect to the volume data.

Once the base line 54 is set, a row of reference cross sections 56 are automatically generated with regard to the volume data 44 corresponding to a three-dimensional space, as shown in FIG. 8. The row of reference cross sections 56 is formed as a plurality of cross sections orthogonal to the base line shown in FIG. 7, and is specifically formed of a plurality of cross sections arranged at equal or non-equal intervals from one end point 50 to the other end point 52. More specifically, the row of reference cross sections 56 includes a plurality of manual tracing reference cross sections 58 and a plurality of automatic tracing reference cross sections 60. The manual tracing reference cross sections 58 are formed in a predetermined number n which is in the range of 5 to 10, for example. When a follow-up addition processing which will be described below is applied, the manual tracing reference cross sections may be additionally set in a number exceeding n. The manual tracing reference cross section corresponds to a representative cross section. Here, because it is sufficient to perform manual tracing only with regard to the representative cross sections, the burden of the user can be significantly lessened. With regard to the individual automatic tracing reference cross sections 60, on the other hand, the tracing lines are automatically generated by interpolation processing, as will be described below.

Figure 9:
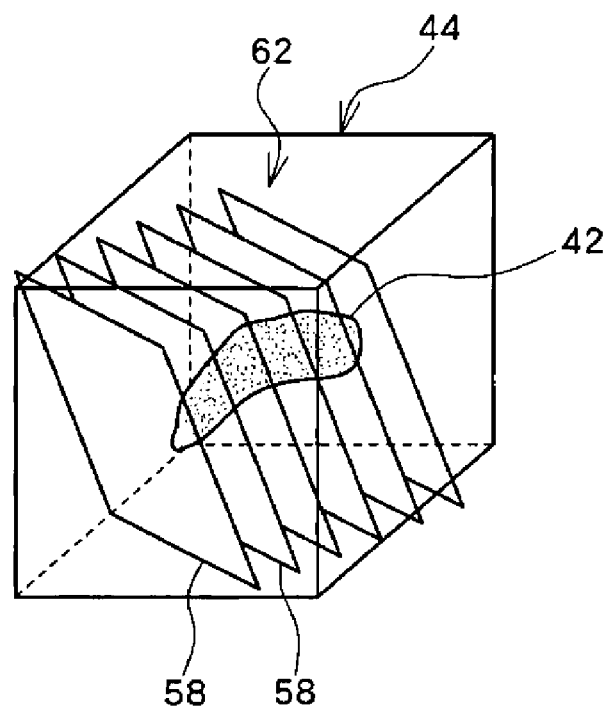
FIG. 9 is a view showing a plurality of manual tracing reference cross sections included in the row of reference cross sections.
Figure 10:
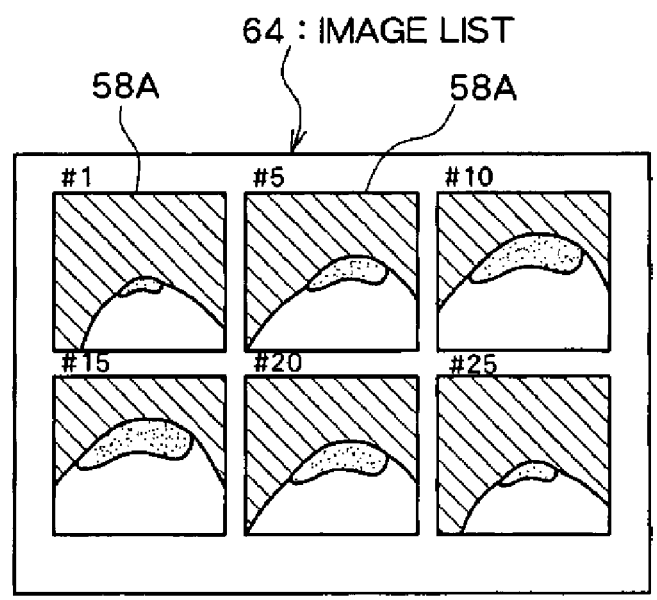
FIG. 10 is a view showing a plurality of tomographic images corresponding to the plurality of manual tracing reference cross sections.

Specifically, in step S105 of FIG. 2, the reference cross sections in the number n which is automatically selected or selected by the user are displayed as a tomographic image on a screen. FIG. 9 shows n reference cross sections 58. FIG. 10 shows a plurality of tomographic images 58A corresponding to the n reference cross sections 58, which form an image list (an image collection) 64. In this case, a plurality of tomographic images 58A may be displayed sequentially one by one or simultaneously displayed.

Figure 11:
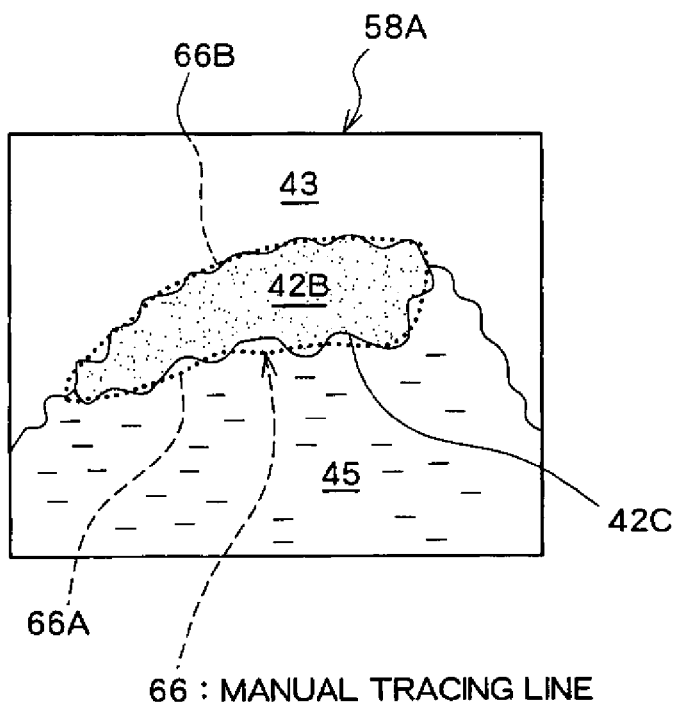
FIG. 11 is a view for explaining a manual tracing line.

In step S106, manual tracing is performed with respect to the individual tomographic images 58A (see FIG. 10). Specifically, the user, while observing an image, traces the outline, i.e. the boundary, of the placenta by using the input section. The result of tracing is shown in FIG. 11. In FIG. 11, numeral 42B denotes a cross section of the placenta, and numeral 42C denotes the outline of the placenta. The outline includes an unclear portion in contact with the uterus and a relatively clear portion in contact with the amniotic fluid. Even an unclear portion can be traced to a certain degree due to human visual judgment and empirical understanding. A manual tracing line denoted by numeral 66 is formed by tracing the outline 42C as a closed loop. The manual tracing line 66 includes a portion 66B located on the uterus 43 side and a portion 66A located on the amniotic fluid 45 side. In the both portions 66A and 66B, precise or faithful tracing cannot be achieved with respect to fine unevenness of the uterus, and only the approximate shape of the uterus is imitated as a loop line.

Figure 12:
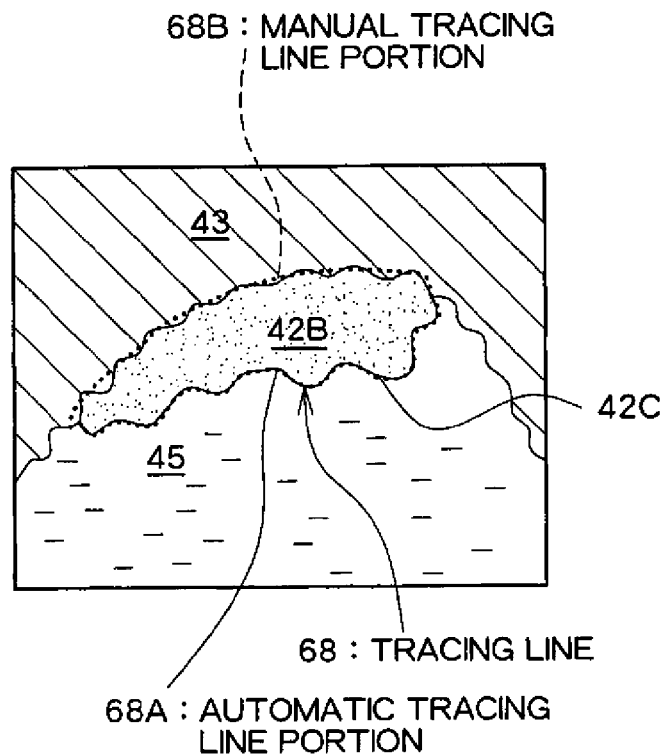
FIG. 12 is a view for explaining automatic correction of the manual tracing line.

In step S107 shown in FIG. 2, automatic correction of the manual tracing line is performed as shown in FIG. 12. This correction processing is performed for each manual tracing line, i.e. for each manual tracing reference cross section serving as a representative cross section. Specifically, as shown in FIG. 12, edge detection processing is applied to each point on the manual tracing line with respect to its peripheral portion, and, with regard to a point for which an edge has been detected, processing of shifting that point to the position on the edge is performed. With regard to a point for which no edge is detected, the manual tracing result is maintained. As such, as a result of the first correction processing performed with respect to each manual tracing line, an automatic tracing line portion 68A obtained by faithful tracing along the outline 42C is formed with regard to the line portion on the amniotic fluid 45 side, as shown in FIG. 12. With regard to the portion of the line on the uterus 43 side, on the other hand, because automatic tracing cannot be appropriately performed due to poor difference in brightness, the original tracing result, which is the manual tracing line 68B, is retained. In this portion, the manual tracing result is preferentially adopted in consideration of errors which could result from automatic tracing due to lack of clarity of the image, although a fine unevenness shape cannot be faithfully traced by the manual tracing. As such, with the above processing, in regards to the manual tracing and the automatic tracing or automatic tracing line correction, it is possible to efficiently use the advantages of the both processing or complement the disadvantages with each other, in consideration of the respective advantages and disadvantages. Further, if the manual tracing is performed on the premise that the automatic tracing line correction is performed, the burden on the user can be advantageously reduced. In addition, an advantage that the precision in extraction and volume calculation can be increased can also be achieved.

Figure 13:
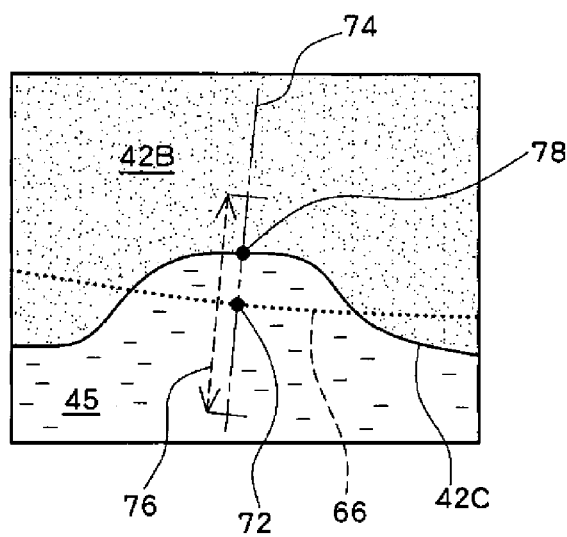
FIG. 13 is a view for explaining automatic correction of a position on the tracing line.

FIG. 13 shows a specific method of correcting a point. With regard to a certain point 72 on the manual tracing line 66, a direction 74 which is orthogonal to the tracing line 66 is defined, and edge detection is executed along this direction 74 in both directions from the point 72. The range of edge detection is indicated by numeral 76. In edge detection, a differential value is calculated at each detection position, and a position is determined to be an edge when the differential value at that position exceeds a predetermined value. In the illustrated example, because the differential value is increased when a detection point reaches the outline 42C, updating processing for shifting the point 72 to a new position 78 is performed. As a result of application of this processing to the individual points on each tracing line, with regard to a portion having a clear outline, a tracing line portion which coincides with the outline can be generated.

While in this embodiment the differential processing is applied as described above, various other processing can also be applied as long as an edge can be detected. According to the present embodiment, because, with regard to an unclear image portion with little difference in brightness, the forced position correction is not performed, i.e. the manual tracing result is preferentially adopted, excessive correction of tracing results can be prevented. Further, the direction of edge detection may be various directions other then the orthogonal direction. For example, when a center point of a tissue is known, a straight line connecting the noted point and the center point may be defined as a detection direction.

Figure 14:
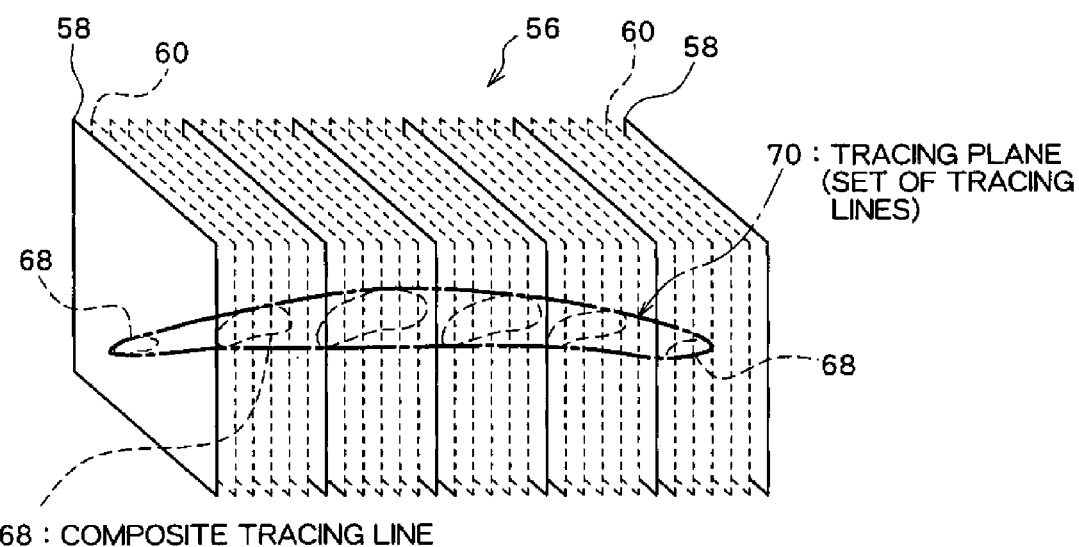
FIG. 14 is a view for explaining a method of generating a plurality of interpolation tracing lines by interpolation processing.

In step S108 shown in FIG. 2, with regard to the plurality of automatic tracing reference cross sections shown in FIG. 8, automatic tracing processing is executed. In this case, as shown in FIG. 14, a plurality of composite tracing lines 68 which are a plurality of manual tracing lines to which the first correction processing has been applied, formed on the plurality of manual tracing reference cross sections 58, are used as a basis. Specifically, on the basis of these composite tracing lines 68, interpolation processing is performed, so that a tracing plane 70 obtained by coupling a plurality of closed loops into a plane shape is formed. In this case, while it is not necessarily required to generate a perfect three-dimensional curved surface, it is at least required that the interpolation processing be executed such that an interpolation tracing line is generated on each automatic tracing reference cross section 60.

Figure 15:
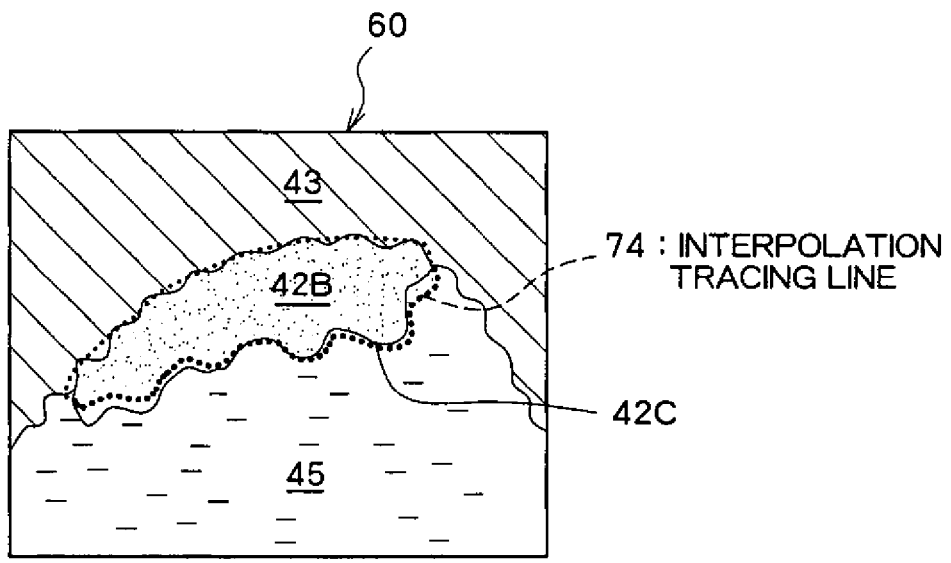
FIG. 15 is a view for explaining an interpolation tracing line generated by interpolation processing.

FIG. 15 shows sectional data 60 on the automatic tracing reference cross section corresponding to a non-representative cross section. Specifically, an interpolation tracing line 74 which is a closed loop substantially enclosing the outline 42C of the placenta 42B which is an object tissue is automatically set. This interpolation tracing line 74, however, is not a result of actual tracing, but is generated by interpolation processing based on two or more composite tracing lines provided on the manual tracing cross sections existing before and after the noted automatic tracing reference cross section. Accordingly, the interpolation tracing line 74 may completely or partially deviate from the actual outline 42C.

Figure 16:
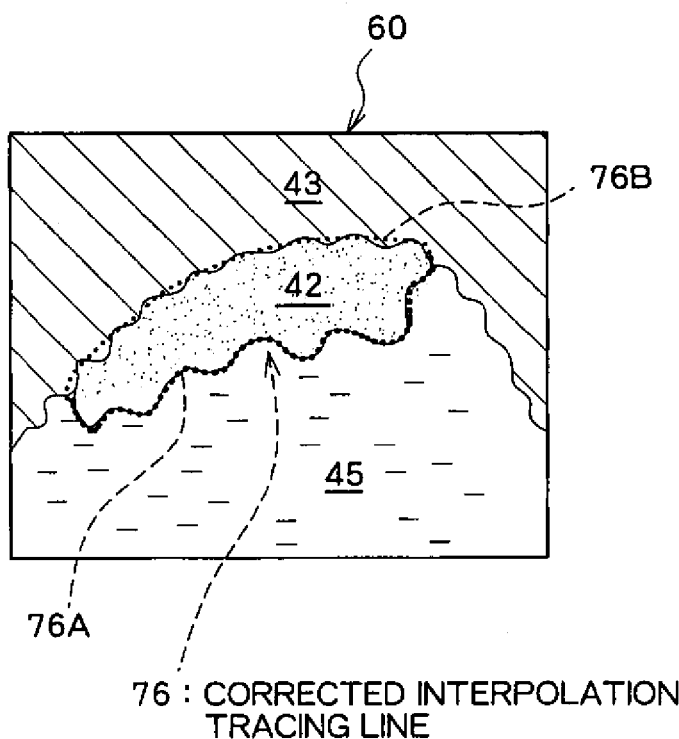
FIG. 16 is a view showing an interpolation tracing line which is automatically corrected.
Figure 17:
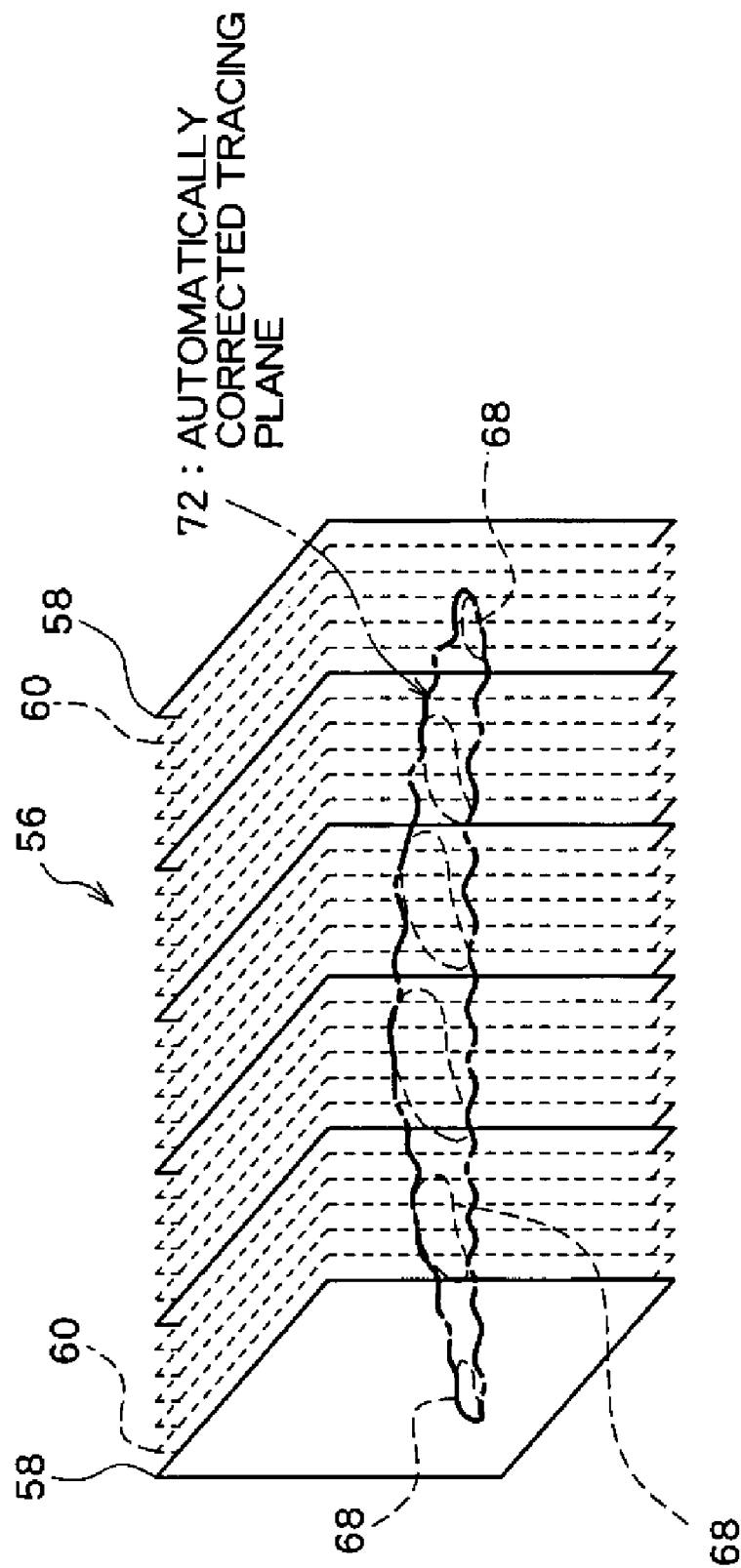
FIG. 17 is a tracing plane formed of a plurality of tracing lines which are set along the entire areas of an object tissue.

Accordingly, in step S109 of FIG. 2, the processing for automatically correcting the tracing lines as described with reference to FIGS. 12 and 13 is executed. Specifically, as shown in FIG. 16, a line portion in contact with the amniotic fluid is subjected to the automatic correction, whereas a line portion in contact with the uterus 43 is not subjected to the automatic tracing correction and the tracing result by means of the interpolation processing is maintained. Consequently, the interpolation tracing line which is partially corrected is formed. The second correction processing as described above is executed with regard to each of the automatic tracing reference cross sections.

By performing a series of the processings described above, a tracing plane having been subjected to the automatic correction, which encloses or imitates the whole placenta which is an object tissue can be defined. The tracing plane 72 is specifically formed of a plurality of closed loops, i.e. a plurality of tracing lines which include the plurality of composite tracing lines (the plurality of manual tracing lines having been subjected to the first correction processing) and the plurality of interpolation tracing lines having been subjected to the second correction processing. In step S111, a three-dimensional image of the tissue which is extracted is displayed on the screen along with the volume data calculated concerning the tissue.

Conventionally, in order to achieve volume calculation with high precision, it is necessary to perform manual tracing precisely with respect to a large number of (such as 200 or 300, for example) cross sections, as a result of which great burden is placed on a user or reliability of the volume calculation value is reduced because such processing is substantially impossible. According to the present embodiment, however, it is sufficient to perform manual tracing only with respect to a plurality of representative cross sections, allowing a significant reduction in the user's burden and also allowing acquirement of the calculation results with high precision. Specifically, because tracing correction is automatically applied to the manual tracing results, a user can perform manual tracing without being concerned with very fine unevenness in the clear outline portions, resulting in a further reduction in the user burden. Further, the manual tracing need not be performed with regard to the non-representative cross sections. Specifically, with regard to the non-representative cross sections, the automatic tracing is applied, and the automatic correction is further applied to the automatic tracing results, thereby processing an image such that the image with high reliability can be obtained. In this regard, the user's burden can also be reduced and highly precise calculation can be performed.

While, in the above example, the base cross section, both end points, the number of representative cross sections, the number of cross sections forming a cross section set, and so on are set by a user, all or a portion of these items may be set automatically. Alternatively, the values of these items may be dynamically varied depending on the situation. Further, while in the above example a plurality of cross sections are basically arranged at an equal interval, it is also possible to reduce the interval between the cross sections, i.e. to arrange the cross sections close to each other in the portion of a tissue in which a change in the shape is great, and to increase the interval between the cross sections, i.e. to arrange the cross sections distant from each other in other portions. Also, according to the above-described embodiment, because whether or not automatic tracing correction is necessary is automatically determined for each point, excessive correction can be prevented. Specifically, it is possible to adaptively determine, in accordance with clearness of the boundary or the outline, whether the manual tracing results or the interpolation tracing results are maintained or these results are corrected. As such, processing which can adapt to various situations can be advantageously achieved. Here, various methods conventionally proposed can be used for automatic tracing and correction of the tracing lines.

Figure 18:
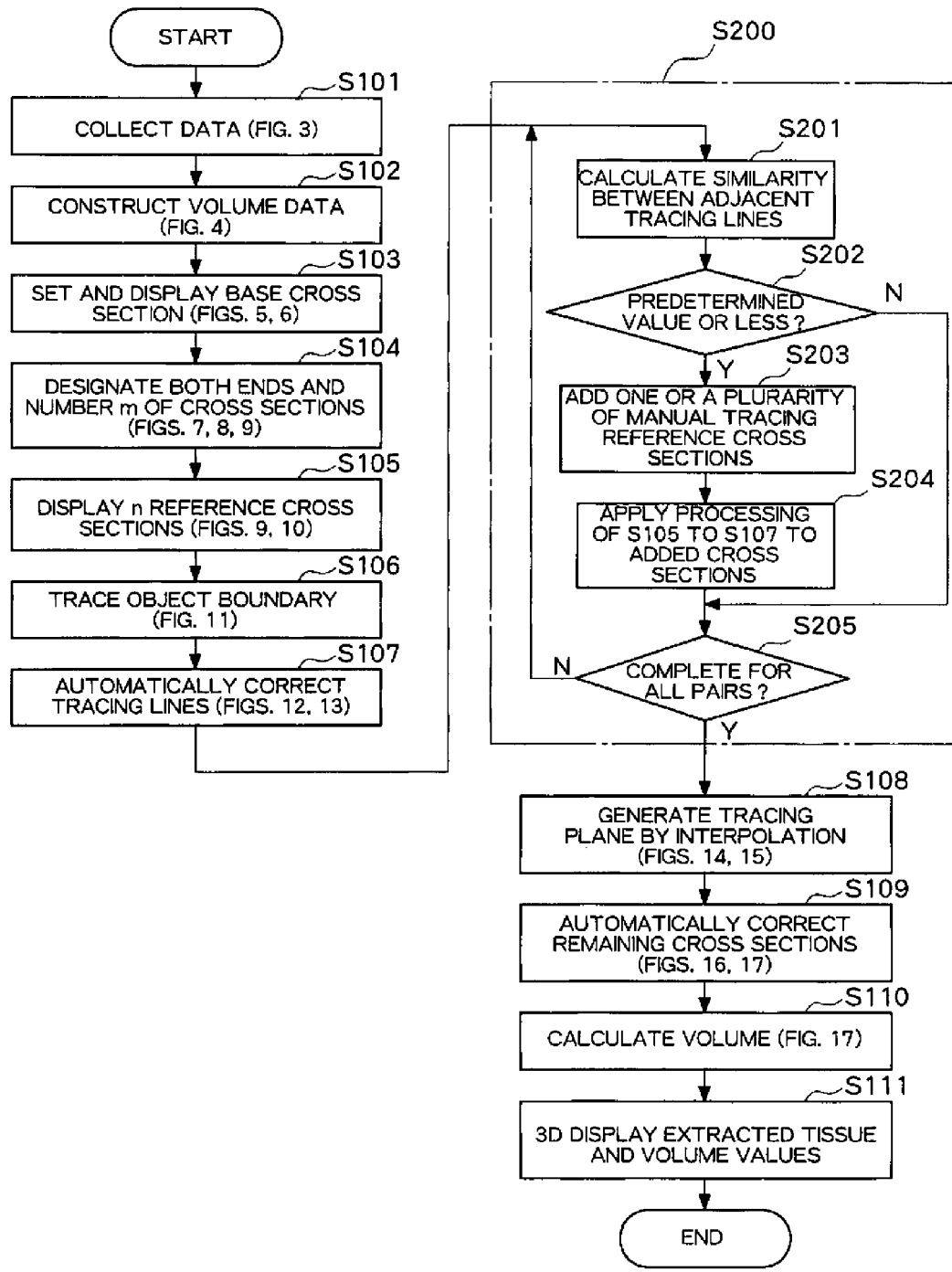
FIG. 18 is a flowchart showing extraction processing according to another embodiment of the present invention.

Referring now to FIGS. 18 to 23, an example modification will be described. FIG. 18 is a flowchart showing a process of extracting an object tissue. It should be noted that steps similar to those shown in FIG. 2 are designated by the same numerals in FIG. 18, and that these steps will not be described again.

Figure 19:
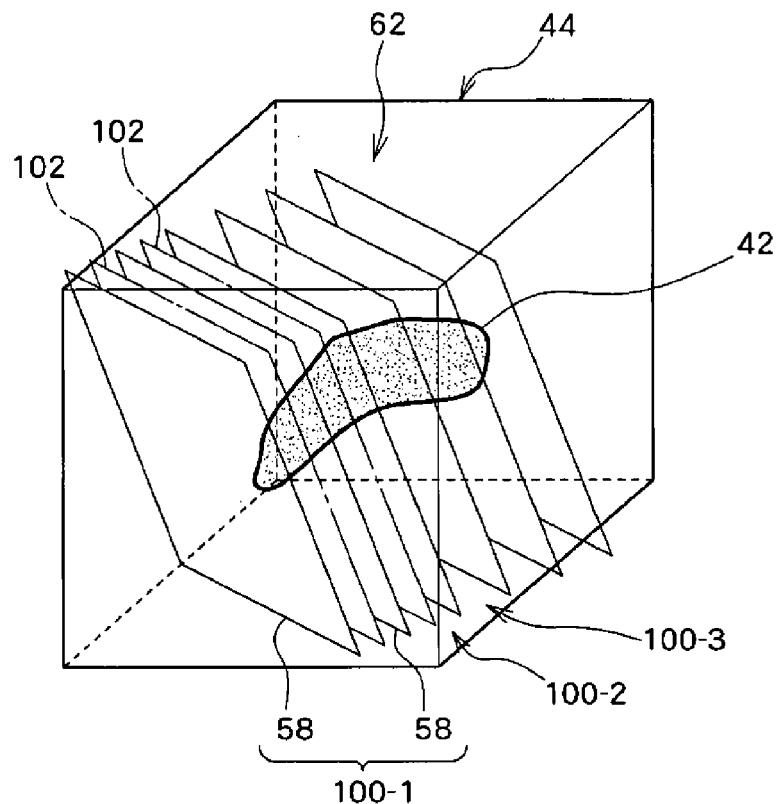
FIG. 19 is a view conceptually showing addition of a manual tracing reference cross section.

The process shown in FIG. 18 further includes step S200 for generating one or a plurality of additional manual tracing reference cross sections (i.e. one or a plurality of additional manual tracing lines) between the steps S107 and S108, as required. This step S200 aims at increasing the density of the manual tracing operations to thus enhance the tissue extraction precision with regard to a portion with a great change in the shape. FIG. 19 conceptually shows the processing content. Specifically, with this processing, when, among pairs of adjacent manual tracing lines 100-1, 100-2, 100-3, . . . , a pair of adjacent manual tracing lines in which a change in the shape of the object tissue portion is great and therefore the similarity of the tracing lines is small is specified, an additional manual tracing reference cross section 102 is additionally set between the specified pairs of adjacent manual tracing lines (see the pairs 100-1 and 100-2 in FIG. 19). Here, in the process shown in FIG. 18, a step corresponding to the addition processing step S200 can be provided between the steps S106 and S107. In this case, after one or a plurality of additional manual tracing lines are added, automatic correction processing (S107) is applied with respect to a group of manual tracing lines including these additional manual tracing lines.

The process shown in FIG. 18 will be specifically described. A series of steps starting from step S201 are performed for each pair of adjacent manual tracing lines, with the object pair of adjacent manual tracing lines being shifted one by one. A pair of adjacent manual tracing lines is formed of two adjacent manual tracing lines (which are two composite tracing lines when automatic correction has been already applied). Assuming that the number of manual tracing reference cross sections prior to the addition processing is n, the pair of adjacent manual tracing lines in the number (n−1) is formed.

In step S201, similarity is calculated with regard to the pair of adjacent manual tracing lines which is under consideration at that time (i.e. an object pair of adjacent manual tracing lines). In calculating the similarity, a cross-correlation operation, for example, is executed. More specifically, information representing the similarity of the shapes of the two manual tracing lines is obtained. This information serves as a criterion when determining whether or not a manual tracing reference cross section should be added, i.e. whether or not a portion has a significant change in the shape.

Figure 20:
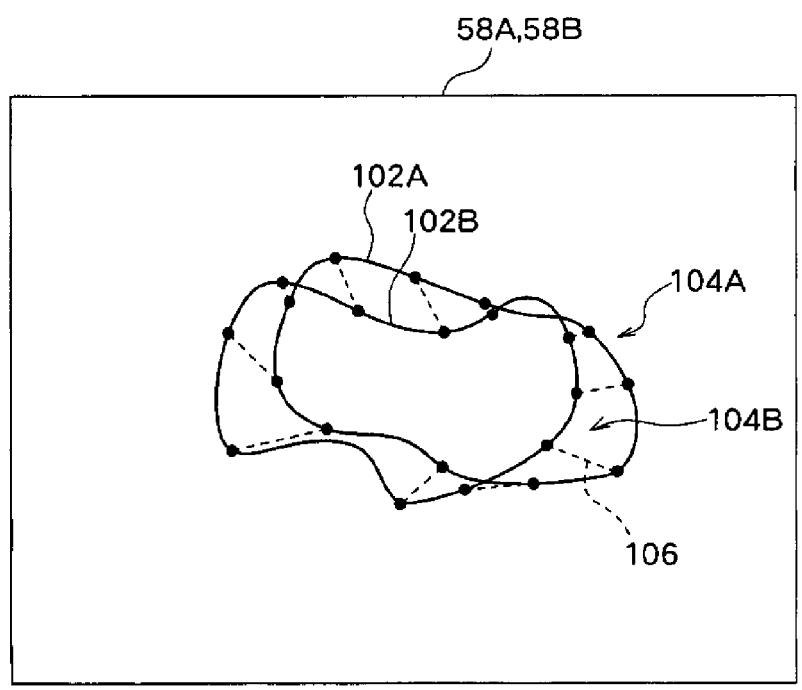
FIG. 20 is a view showing a relationship of the shapes of a pair of adjacent manual tracing lines.

FIG. 20 shows a specific example of similarity calculation. First, in order to appropriately perform pairing which will be described below, sampling processing is applied to each of two manual tracing lines 102A and 102B which are adjacent to each other, to thereby set rows of points 104A and 104B, respectively. Then, a plurality of point pairs are defined between these rows of points 104A and 104B in accordance with a predetermined rule. Specifically, each point pair is formed of two points which are in a corresponding relationship (see numeral 106). A variety of suitable rules can be selectively adopted in accordance with the situation. For example, it is possible that, with regard to the rows of points 104A and 104B, a first point pair is specified for two points which are the most closely adjacent to each other, and then pairing is sequentially performed from the first point pair in the predetermined rotating direction, to finally specify the n-th point pair.

Figure 21:
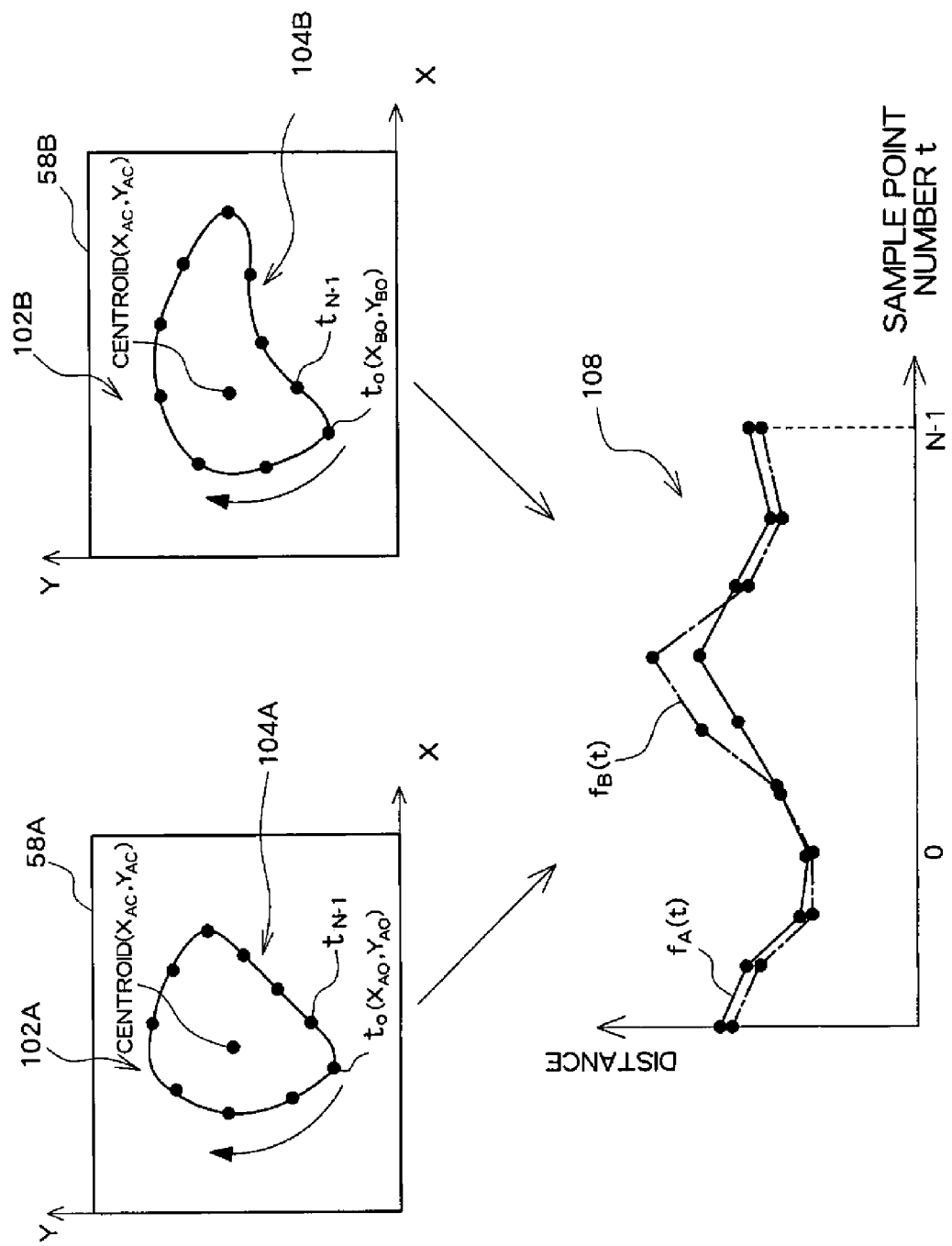
FIG. 21 is a view for explaining a method of calculating similarity between a pair of adjacent manual tracing lines.

FIG. 21 shows a result of such processing. Specifically, as described above, two rows of points 104A and 104B are set on the two manual tracing lines 102A and 102B on the two adjacent manual tracing reference cross sections 58A and 58B, respectively. Then, a centroid is obtained with regard to each of the manual tracing lines 102A and 102B, and a distance between the centroid and each point is calculated. As indicated by numeral 108 in FIG. 21, when the distance to the centroid is represented for each sample point number t with respect to each row of points 104A, 104B, graphs (functions) $f_A(t)$ and $f_B(t)$ are obtained. Then, by executing the cross-correlation operation (1) described below, the similarity a as a cross-correlation coefficient can be obtained (similarity α: 0.0 to 1.0). Here, the method of obtaining the similarity α is not limited to the example described above. In any case, information indicating the similarity of shapes between two tracing lines is obtained.

$$\alpha = \frac{\int_0^{N-1} f_A(t) f_B(t) dt}{\sqrt{\int_0^{N-1} f_A^2(t) dt} \sqrt{\int_0^{N-1} f_B^2(t) dt}} \quad (1)$$

Referring again to FIG. 18, in step S202, whether or not the similarity α described above is equal to or less than a predetermined value is determined. If the similarity α exceeds the predetermined value, the two shapes are determined to be similar, and the process proceeds to step S205 and addition of cross sections is not performed. If the similarity α is equal to or less than the predetermined value, on the other hand, the two shapes are determined to have no similarity, i.e. a change in the shape of the object tissue is determined to be great. Consequently, in step S203, one or a plurality of additional manual tracing reference cross sections are set between the two adjacent manual tracing reference cross sections. Here, the number of cross sections to be added may be one fixed number or may be varied depending on the situation. Subsequently, the processing similar to those in steps S105 to 107 described above is applied on each of the added manual tracing reference cross sections. More specifically, each of the added reference cross section is displayed as an image, and the user performs manual tracing while observing the image. Then, each manual tracing line is automatically corrected. Here, such an additional manual tracing operation may be performed after completion of the determination of necessity of addition with respect to all the pairs of adjacent manual tracing lines. In step S205, whether or not the above-described determination concerning the addition processing and the necessary addition processing is completed is determined with regard to all the pairs of adjacent manual tracing lines, and if there are any unprocessed pairs of adjacent manual tracing lines, the above processing is repeated with respect to these unprocessed pairs.

Figure 23:
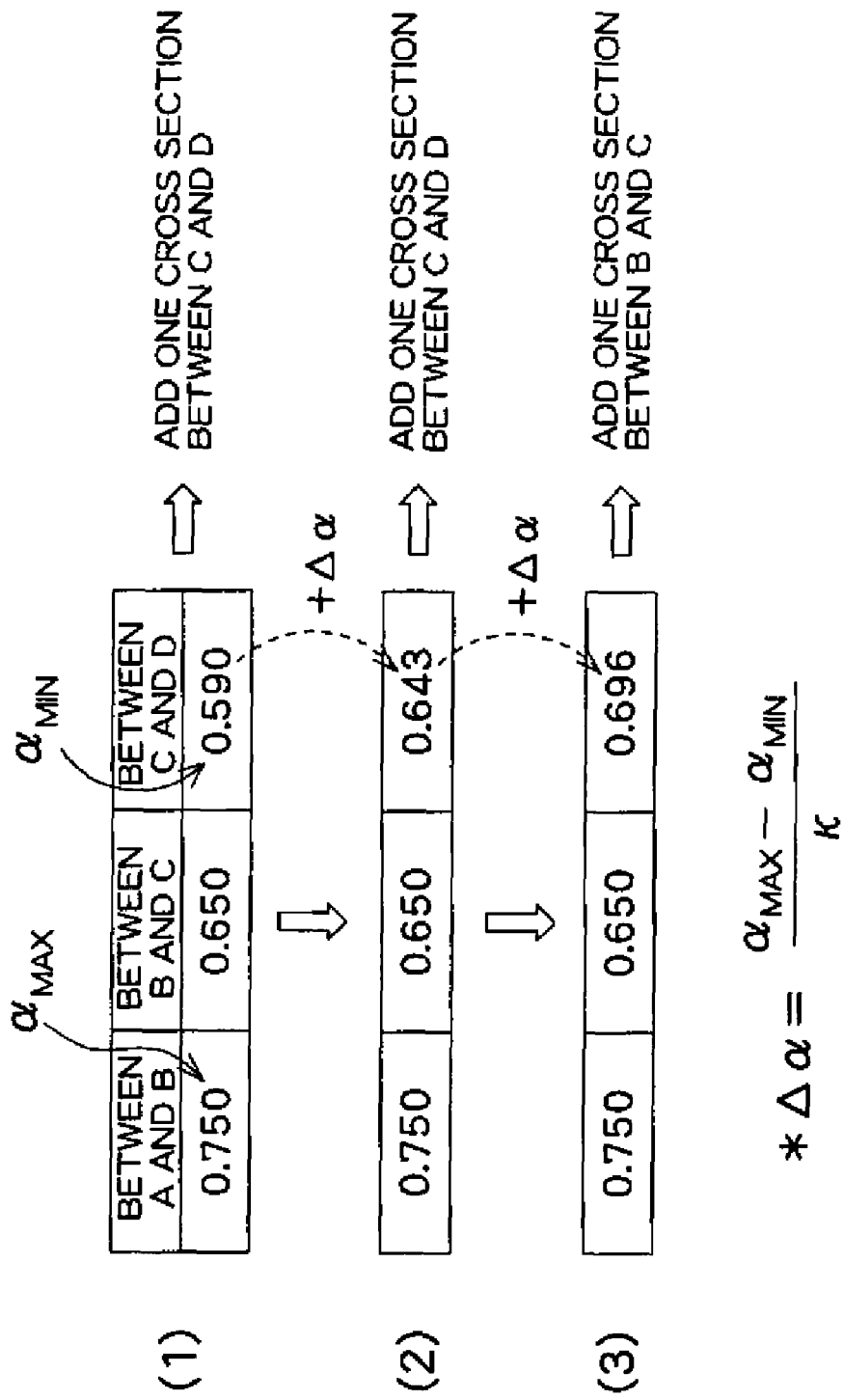
FIG. 23 is a view for specifically explaining the method shown in the lower portion of FIG. 22.

With regard to the above-described step S203, several methods of adding a manual tracing reference cross section may be applied, as will be described below with reference to FIGS. 22 and 23. It should be noted that the correction of the process shown in FIG. 18 should be determined based upon the addition method to be employed.

FIG. 22 shows three types of addition methods. When the method shown in the upper level of the table shown in FIG. 22 is selected, a single predetermined value (threshold value) described above is used. Then, when the similarity a equals to or is less than the predetermined value, only one manual tracing reference cross section is added. FIG. 22, in the upper level, further shows the condition and specific example of this method. In this specific example, one reference cross section is added in each of a space between the cross sections B and C and a space between the cross sections C and D (see the hatched portions). In the type of method shown in the middle level in the table of FIG. 22, a plurality of different threshold values are used. For example, a plurality of threshold values are used as indicated as conditions in the table, and either 1, 2, or 3 is selected as the number of cross sections to be added for each range of the threshold values. Obviously, no reference cross sections are to be added if the similarity exceeds the maximum threshold value. In the specific example of this method, one reference cross section is added between B and C, and two reference cross sections are added between C and D. Further, in the type of method shown in the lower level in the table of FIG. 22, the number of cross sections to be added is previously determined as k, and the additional cross sections in the number k are dynamically distributed. This method will be described with reference to FIG. 23. It is first assumed that an increment $\Delta\alpha$ has been obtained from $(\alpha_{MAX}-\alpha_{MIN})/k$. Here, $\alpha_{MAX}$ indicates the maximum value of all the $\alpha$ values in its initial state, and $\alpha_{MIM}$ indicates the minimum value of all the $\alpha$ values in its initial state. As shown in FIG. 23 (1), a cross section pair having $\alpha$ with the minimum value is specified among all the cross section pairs, and one additional cross section is inserted. In this example, insertion of one additional cross section between C and D is determined. With this processing, the increment $\Delta\alpha$ described above is added to the minimum $\alpha$ (i.e. the original $\alpha$ between C and D) (at this point in time, the minimum value is raised). Then, as shown in FIG. 23(2), in the state after the above-descried addition processing, $\alpha$ having the minimum value is specified again. Here, because the $\alpha$ value between C and D is minimum once again, further insertion of one additional cross section between C and D is determined. Then, as in the above processing, the increment $\Delta\alpha$ is further added to a having been subjected to adding correction. Subsequently, as shown in FIG. 23(3), in the state after the second addition processing, $\alpha$ with the minimum value is specified. In this case, because $\alpha$ between B and C is the minimum, insertion of an additional cross section between B and C is determined. In this manner, with repetition of insertion of an additional cross section in k times, the insertion processing of additional cross sections is completed. The processing conditions and the specific example in this case are also shown in the lower level in the table of FIG. 22. While example adding methods are described above, any appropriate method may be selected in accordance with a particular situation. The method shown in the lower level of the table in FIG. 22 is advantageous in that a further number of cross sections can be added in the position where the cross sections should be preferentially added, within a limited number of cross sections to be added. According to the methods shown in the upper and middle levels, on the other hand, simple processing can be expected.

While the preferred embodiments of the present invention have been described using specific terms, such description is for illustrative purposes only, and it is to be understood that changes and variations may be made without departing from the spirit or scope of the appended claims.

What is claimed is:

1. An ultrasound diagnostic apparatus, comprising:
   a data acquisition section configured to perform transmission and reception of ultrasound with respect to a three-dimensional space including an object tissue to acquire volume data;
   a representative cross section processing section configured to apply, after a plurality of manual tracing lines are formed on a plurality of representative cross sections which are set with regard to the object tissue, a first correction processing to each manual tracing line;
   a non-representative cross section processing section configured to form, by interpolation processing based on the plurality of manual tracing lines to which the first correction processing has been applied, respective interpolation tracing lines on each of a plurality of non-representative cross sections which are set with regard to the object tissue, and configured to apply a second correction processing to each interpolation tracing line; and
   a unit configured to extract object tissue data from the volume data or configured to calculate a volume of the object tissue, based on rows of tracing lines formed of the plurality of manual tracing lines to which the first correction processing has been applied and the plurality of interpolation tracing lines to which the second correction processing has been applied.

2. The ultrasound diagnostic apparatus according to claim 1, wherein the representative cross section processing section includes:
   a selection section configured to select the plurality of representative cross sections from a set of cross sections which is set with respect to the object tissue;
   a unit configured to receive a tracing input from a user with respect to each representative cross section which is selected; and
   a first correction processing section configured to determine, for the first correction processing, whether or not correction can be applied for each point on each manual tracing line and to correct a position of a point which is determined to be correctable based on an actual tissue outline.

3. The ultrasound diagnostic apparatus according to claim 2, wherein
   the first correction processing section is configured to determine whether or not correction can be performed by setting a cross line with regard to each point and performing edge detection on the cross line.

4. The ultrasound diagnostic apparatus according to claim 1, wherein the non-representative cross section processing section includes:
   a unit configured to form the respective interpolation tracing lines on each of the plurality of non-representative cross sections by interpolation processing based on the plurality of manual tracing lines to which the first correction processing has been applied; and
   a second correction processing section configured to determine, for the second correction processing, whether or not correction can be performed for each point on each interpolation tracing line and to correct a position of a point which is determined to be correctable based on an actual tissue outline.

5. The ultrasound diagnostic apparatus according to claim 4, wherein
   the second correction processing section is configured to determine whether or not correction can be performed by setting a cross line with regard to each point and performing edge detection on the cross line.

6. The ultrasound diagnostic apparatus according to claim 1, further comprising:
   a unit configured to receive designation of a base line extending through the object tissue; and
   a unit configured to set a set of cross sections which are arranged in a direction of the base line and which are orthogonal to the base line, wherein the plurality of representative cross sections and the plurality of non-representative cross sections are determined from the set of cross sections.

7. The ultrasound diagnostic apparatus according to claim 1, wherein the object tissue is a tissue within a uterus.

8. The ultrasound diagnostic apparatus according to claim 1, further comprising:
- a similarity calculation section configured to calculate a similarity value for each pair of adjacent manual tracing lines in the plurality of manual tracing lines before or after the first correction processing;
- an additional representative cross section setting section configured to add one or a plurality of additional representative cross sections in addition to the plurality of representative cross sections based on the similarity value for each pair of adjacent manual tracing lines;
- an input section configured to form one or a plurality of manual tracing lines on the one or plurality of additional representative cross sections;
- an additional representative cross section processing section configured to apply the first correction processing to the one or a plurality of manual tracing lines formed on the one or plurality of additional representative cross sections.

9. The ultrasound diagnostic apparatus according to claim 8, wherein
the similarity calculation section is configured to calculate the similarity value by performing cross correlation operation between the two manual tracing lines forming each pair of adjacent manual tracing lines.

10. The ultrasound diagnostic apparatus according to claim 8, wherein
the additional representative cross section setting section is configured to add the one or plurality of additional representative cross sections between a pair of adjacent representative cross sections for which the similarity value satisfies a predetermined addition condition.

11. The ultrasound diagnostic apparatus according to claim 10, wherein
the additional representative cross section setting section is configured to determine the number of additional representative cross sections to be added in accordance with the similarity value.

12. A volume data processing method, comprising:
- storing volume data acquired by performing transmission and reception of ultrasound with respect to a three-dimensional space including an object tissue;
- setting a plurality of representative cross sections with regard to the object tissue;
- forming respective manual tracing lines on the plurality of representative cross sections which are set with regard to the object tissue;
- setting a plurality of non-representative cross sections with regard to the object tissue;
- forming respective interpolation tracing lines on each of the plurality of non-representative cross sections;
- performing correction processing by determining whether or not position correction can be performed, based on an actual tissue outline, with regard to each point on each manual tracing line formed on each of the representative cross sections and each point on each interpolation tracing line formed on each of the non-representative cross sections which are set with regard to the object tissue and correcting a position of a point which is determined to be correctable; and
- extracting the object tissue or calculating a volume of the object tissue based on a row of a plurality of interpolation tracing lines and a plurality of manual tracing lines to which the correction processing has been applied.

13. A volume data processing method, comprising:
- storing volume data obtained by performing transmission and reception of ultrasound with respect to a three-dimensional space including an object tissue;
- setting a plurality of representative cross sections with regard to the object tissue;
- forming respective manual tracing lines on the plurality of representative cross sections which are set with regard to the object tissue;
- setting one or a plurality of additional representative cross sections in addition to the plurality of representative cross sections;
- respectively forming one or a plurality of manual tracing lines on the one or a plurality of additional representative cross sections;
- setting a plurality of non-representative cross sections with regard to the object tissue;
- forming respective interpolation tracing lines on the plurality of non-representative cross sections;
- performing correction processing by determining whether or not position correction can be performed, based on an actual tissue outline, with regard to each point on each manual tracing line formed on each of the representative cross sections, each point on each manual tracing line formed on each of the additional representative cross sections, and each point on each interpolation tracing line formed on each of the non-representative cross sections which are set with regard to the object tissue and correcting a position of a point which is determined to be correctable; and
- extracting the object tissue or calculating a volume of the object tissue based on a row of a plurality of interpolation tracing lines and a plurality of manual tracing lines to which the correction processing has been applied.

* * * * *